United States Patent
Kawachi et al.

[11] Patent Number: 6,136,608
[45] Date of Patent: Oct. 24, 2000

[54] METHOD FOR DETERMINING FORMALDEHYDE PRESENT IN AIR

[75] Inventors: Takeshi Kawachi, Tokorozawa; Masahiro Moriya, Kiyose; Yasue Sato, Chofu, all of Japan

[73] Assignee: Obayashi Corporation, Japan

[21] Appl. No.: 09/125,827

[22] PCT Filed: Dec. 24, 1997

[86] PCT No.: PCT/JP97/04863

§ 371 Date: Apr. 5, 1998

§ 102(e) Date: Apr. 5, 1998

[87] PCT Pub. No.: WO98/30897

PCT Pub. Date: Jul. 16, 1998

[30] Foreign Application Priority Data

| Jan. 7, 1997 | [JP] | Japan | 9-000636 |
| Oct. 13, 1997 | [JP] | Japan | 9-278617 |

[51] Int. Cl.⁷ ........................... G01N 31/22
[52] U.S. Cl. ............. 436/130; 436/128; 436/166; 436/167; 422/86
[58] Field of Search ............ 436/128, 130, 436/166, 167; 422/86

[56] References Cited

U.S. PATENT DOCUMENTS

| 4,511,658 | 4/1985 | Lambert et al. | 436/130 |
| 5,637,505 | 6/1997 | Li et al. | 436/11 |

FOREIGN PATENT DOCUMENTS

| 2809475 | 9/1979 | Germany. |
| 50-62694 | 5/1975 | Japan. |
| 50-118785 | 9/1975 | Japan. |
| 54-36791 | 3/1979 | Japan. |
| 60-170756 | 9/1985 | Japan. |
| 63-221235 | 9/1988 | Japan. |
| 64-33063 | 3/1989 | Japan. |
| 64-53944 | 4/1989 | Japan. |
| 4-51648 | 4/1992 | Japan. |
| 5-26789 | 2/1993 | Japan. |
| 6-43144 | 2/1994 | Japan. |
| 6-117977 | 4/1994 | Japan. |
| 6-174705 | 6/1994 | Japan. |
| 6-221970 | 8/1994 | Japan. |

OTHER PUBLICATIONS

Japanese Industrial Standard, "Methods for determination of formaldehyde in flue gas," K 0303–1993, UDC 543,274:547.281.1, month unavailable.

Dickinson et al., J. Chem. Soc. Perkins Trans. I, 10, pp. 975–979. month unknown 1975.

Durst et al., J. Chem. Educ., 55, p. 206, month unknown 1978.

Analytical Chemistry, vol. 46, No. 2 (1974) pp: 298–299, N.W. Jacobson and R.G. Dickinson, "*Spectrometric Assay of Aldehydes as 6–Mercapto–3–substituted–s–triazolo(4, 3–b)–s–tetrazines*".

*Primary Examiner*—Robert J. Warden, Sr.
*Assistant Examiner*—Kaj K. Olsen
*Attorney, Agent, or Firm*—Morrison & Foerster

[57] ABSTRACT

The concentration of formaldehyde in air is measured by the method of the invention. More specifically, the invention relates to a method for analyzing formaldehyde in air by collecting the air and implementing an analysis of the concentration of formaldehyde at the site where such air is found.

18 Claims, 5 Drawing Sheets

UPON GAS COLLECTION ←——
UPON DISCHARGE ←----

(a)          (b)

METHOD FOR DETERMINING FORMALDEHYDE PRESENT IN AIR

TECHNICAL FIELD

The present invention relates to a method for analyzing formaldehyde. More specifically, the invention relates to a method for analyzing formaldehyde in the ambient air by collecting formaldehyde gas and simply implementing an analysis of concentration thereof.

BACKGROUND ART

In recent years, it has been pointed out that toxic gas having harmful influence on a human body is discharged from various new building materials employed in dwelling houses and so forth. Formaldehyde gas has been listed as one of such toxic gases. Therefore, demand for collection of the formaldehyde gas in the ambient air and analysis of formaldehyde concentration is becoming greater.

The basic principle of the analysis of formaldehyde concentration well known in the art is as follows. Formaldehyde (HCHO) and AHMT (4-amino-3-hydrazino-5-mercapto-1,2,4-triazole) react under alkaline condition to form a product which indicates a red color when oxidized by $KIO_4$ (potassium periodate). The density of this color development is in proportion to the concentration of the formaldehyde. Therefore, an analytical curve for performing the analysis of the unknown sample is prepared with respect to the relation between light transmittance (absorbance) in the vicinity of wavelength 550 nm and concentration of formaldehyde. The standard operating procedure is as follows.

① A given amount of the sample solution into which the formaldehyde is admixed, is measured by means of a pipette and filled into a glass vessel.

② A given amount of alkaline reagent is measured by means of a pipette and added to the glass vessel.

③ A given amount of AHMT reagent is measured by means of a pipette and added to the glass vessel, and left for about 20 minutes while mixing.

④ A given amount of $KIO_4$ reagent is measured by means of the pipette and added to the glass vessel.

⑤ After transferring to a color comparison tube, the color development density of the resultant solution is measured by means of a colorimeter or a spectrophotometer.

⑥ The operations of ① to ⑤ are performed by using standard solutions (a few of which have different concentrations) containing a known amount of formaldehyde, respectively to prepare an analytical curve.

⑦ The formaldehyde concentration contained in the sample solution is derived by comparison with the analytical curve.

In addition, the formaldehyde concentration in the ambient air can be converted by the following equation, $$Cv = Cl \times (A \times 22.4)/(B \times M \times Q)$$

wherein,

Cv: HCHO concentration in the ambient air (ppm)
Cl: HCHO content contained in an aliquot portion of liquid ($\mu$g)
A: Collecting liquid amount (ml).
B: Amount of the aliquot portion of liquid (ml)
M: Molecular weight of HCHO
Q: Air suction amount (l)

However, according to the conventional method for analyzing formaldehyde set forth above, since the analyzing operation becomes extremely complicated, it is necessary to take the formaldehyde collected in the building site back to a location where an analyzing equipment is organized and implement the analysis of concentration. Therefore, the result of the analysis cannot be obtained at the site where the gas is collected, causing the possibility of delay in judgement and assessment. Meanwhile, the condition of the sample may also be changed by transportation of the collected sample, by transferring of vessels, and during storage until analysis implementation, all of which may create a situation in which accurate data cannot be obtained.

Furthermore, since a knowledge in chemistry is required for the calculation of the concentration, and since close attention becomes necessary upon handling the chemicals for analysis, analysis cannot be implemented except by a skilled person in chemical analysis. By this, problems such as long-time requirement and high cost by relying on an analyzing organization or the like are apt to arise.

DISCLOSURE OF THE INVENTION

The object of the present invention is to provide a method for analyzing formaldehyde in the ambient air, by which accurate measurement is enabled with simple operation, at low cost, without skill requirement, and within a short period of time in the building site.

A method for analyzing formaldehyde in the ambient air according to the present invention, comprises the steps of:

passing a given amount of air to be inspected through a collecting vessel filled with a given amount of 2N—KOH solution;

filling a given amount of AHMT reagent into the collecting vessel and leaving the reagent for a given amount of time;

setting a standard color solution to an absorptiometer for adjusting the indication value thereof to a predetermined value; and adding a given amount of $KIO_4$ reagent to the collecting vessel, setting the collecting vessel to the absorptiometer, and detecting formaldehyde concentration from the indication value of the absorptiometer.

In this case, it is preferable that the composition of the AHMT reagent may be AHMT:1%, and HCl:1 mol/liter, and the composition of the $KIO_4$ reagent may be $KIO_4$:1% and KOH:0.25N.

A method for analyzing formaldehyde in the ambient air according to the present invention comprises the steps of:

passing a given amount of air to be inspected through a collecting vessel filled with a given amount of 2N—NaOH solution;

filling a given amount of AHMT reagent prepared by using $HClO_4$ into the collecting vessel and leaving the reagent for a given amount of time;

setting a standard color solution to an absorptiometer for adjusting the indication value thereof to a predetermined value; and adding a given amount of $KIO_4$ reagent to the collecting vessel, setting the collecting vessel to the absorptiometer, and detecting formaldehyde concentration from the indication value of the absorptiometer.

In this case, it is preferable that the composition of the AHMT reagent may be AHMT:1% and $HClO_4$:4 to 5%, and the composition of the $KIO_4$ reagent is $KIO_4$:1% and KOH:0.2 to 0.3N.

The collecting vessel may be filled with 2.0 ml or less of the 2N—KOH solution or 2N—NaOH solution.

The collecting vessel is to be filled with substantially about 0.5 ml of the AHMT reagent and the $KIO_4$ reagent, whether 2N—KOH solution or 2N—NaOH solution is used.

Furthermore, the standard color solution may be a standard colored liquid prepared by using a red color dye having a color density corresponding to a color development density caused upon reaction of a known amount of formaldehyde with the reagent, whether 2N—KOH solution or 2N—NaOH solution is used.

A method for analyzing formaldehyde in the ambient air according to the present invention comprises the steps of:

passing a given amount of air to be inspected through a collecting vessel filled with collecting liquid prepared by adding a given amount of AHMT solution to a given amount of 2N—KOH solution, or with a collecting liquid prepared by adding a given amount of AHMT solution prepared by using $HClO_4$ solution to a given amount of 2N—NaOH solution;

setting a standard color solution to an absorptiometer for adjusting the indication value thereof to a predetermined value; and setting the collecting vessel to the absorptiometer, and detecting formaldehyde concentration from the indication value of the absorptiometer.

According to the method for analyzing formaldehyde in the ambient air according to the present invention mentioned as set forth above, formaldehyde gas in the ambient air can be efficiently collected by 2N—KOH solution or 2N—NaOH solution by passing air being inspected through a collecting vessel filled with 2N—KOH solution or 2N—NaOH solution.

By the use of AHMT reagent and $KIO_4$ reagent necessary for analysis, an optimal reaction condition is obtained with respect to 2N—KOH solution or 2N—NaOH solution.

Especially, since $HClO_4$ is used for dissolving the AHMT reagent, corrosion of the injection needle and contamination of the reagent can both be avoided when employing 2N—NaOH solution. Further, since 2N—NaOH is employed as the collecting liquid considering that $HClO_4$ is used for AHMT reagent, it is possible to prevent the sample solution from causing white turbidity.

The standard colored liquid is prepared corresponding to the color development density developed upon reaction of a known amount of formaldehyde with a reagent, and it is employed as a standard color solution. By adjusting the absorptiometer by using the absorbance of the standard colored liquid as a standard upon absorbance measurement, it becomes unnecessary to prepare an analytical curve by actually performing reaction of the known amount of the formaldehyde liquid upon each analysis.

Since the absorptiometer is adjusted by setting the indication value of the standard colored liquid to a predetermined value under a premise that a given amount of the air passes through the reaction vessel, the indication value of the unknown sample can be directly read as the concentration of the formaldehyde upon measurement of absorbance. Accordingly, calculation using molecular weight and volume conversion coefficients as gas and so forth of the formaldehyde becomes unnecessary.

Therefore, when performing the analysis of formaldehyde, no special device is required to obtain the results within a short period and at the site where the gas is collected. Also, expert knowledge and chemical calculation becomes unnecessary. Further, transferring or division of sampled solution becomes unnecessary, and special measuring equipment for chemical analysis, which requires skill in handling, are not necessary.

On the other hand, in case of using the 2N—KOH solution, the AHMT reagent is prepared to have a composition of AHMT:1%, and HCl:1 mol/liter, and the $KIO_4$ reagent is prepared to have a composition of $KIO_4$:1% and KOH:0.25N, and in case of 2N—NaOH solution, the AHMT reagent is prepared to have a composition of AHMT:1% and $HClO_4$:4 to 5%, and the $KIO_4$ reagent is prepared to have a composition of $KIO_4$:1% and KOH:0.2 to 0.3N. Accordingly, the AHMT reagent and $KIO_4$ reagent necessary for analysis can be set so that optimal reaction condition is obtained with respect to the 2N—KOH solution or 2N—NaOH solution.

The amount of 2N—KOH solution or 2N—NaOH solution used is small as 2.0 ml or less, so that high condensation can be achieved even with small suction amount of air to facilitate detection even in low gas concentration. This is an appropriate concentration for certainly maintaining the reactivity of the AHMT reagent which is added afterwards, and thus, it becomes unnecessary to add alkaline reagents which were used conventionally.

Furthermore, the collecting vessel is to be filled with substantially about 0.5 ml of the AHMT reagent and the $KIO_4$ reagent whether 2N—KOH solution or 2N—NaOH solution is used. Since the amount of both reagents used at one time is small, analyses can be implemented many times even when the amounts of the reagents carried are small. By setting the adding amount of both reagents to be appropriate at 0.5 ml, the possibility of deterioration in detection sensitivity can be avoided. This problem was caused because conventionally a solution with lower concentration was used, which required about four times of adding amount and which lowered color development because of increase in overall liquid amount. On the other hand, the possibility of increase in reading error of liquid amount upon measurement using an injector can be avoided when the adding amount of the reagent is extremely reduced.

Furthermore, the standard colored liquid, prepared by using a red color dye corresponding to a color development density upon reaction of a known amount of formaldehyde with a reagent, is employed as the standard color solution. Therefore, since the colorimeter (absorptiometer) is adjusted by using the absorbance of the standard colored liquid as a standard upon absorbance measurement, it becomes unnecessary to prepare an analytical curve by actually performing a reaction using a known amount of the formaldehyde liquid for each analysis. Also, if the standard colored liquid is prepared by using a red color dye, it is possible to avoid fading of the color development and also possible to avoid the color of the liquid from gradually turning dilute and unstable according to elapsed time.

Furthermore, a method for analyzing formaldehyde in the ambient air according to the present invention may comprise the following simplified steps of: passing a given amount of air to be inspected through a collecting vessel filled with a collecting liquid prepared by adding a given amount of AHMT solution to a given amount of 2N—KOH solution, or otherwise a collecting liquid prepared by adding a given amount of AHMT solution prepared using $HClO_4$ to a given amount of 2N—NaOH solution; setting a standard color solution to an absorptiometer for adjustment of the indication value to a predetermined value; setting the collecting vessel to the absorptiometer; and detecting formaldehyde concentration from the indication value. By this, it is possible to perform the analyzing operation very simply.

DETAILED DESCRIPTION OF THE INVENTION

Figure 1:
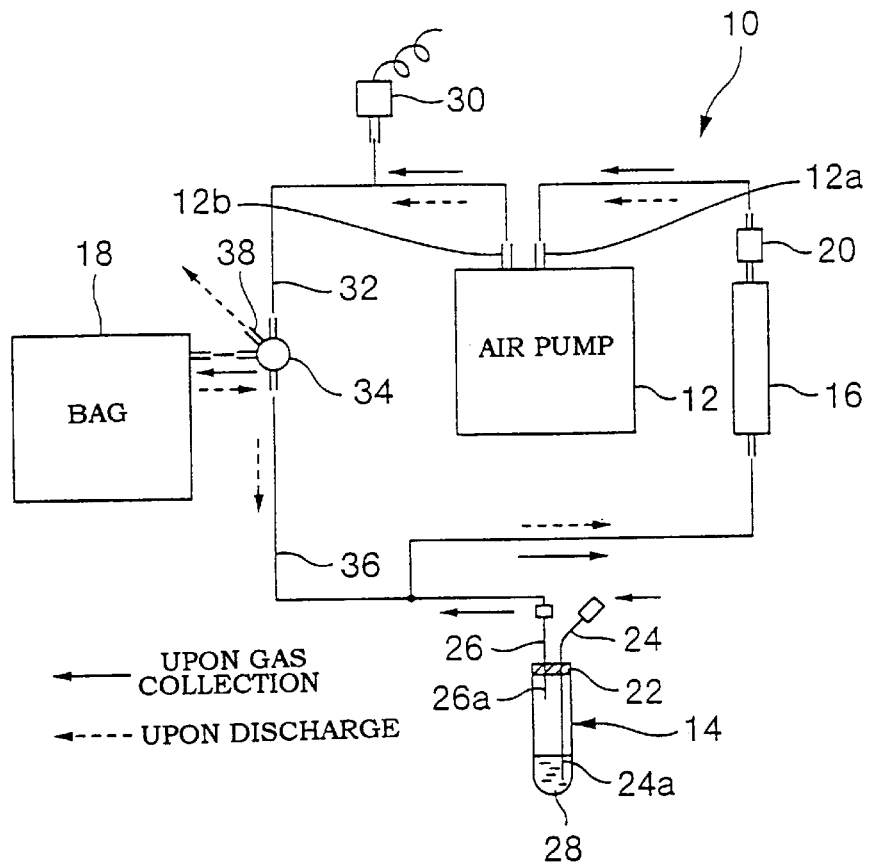
FIG. 1 is a circuit diagram of one embodiment of a gas collecting system applicable to a method for analyzing formaldehyde in the ambient air according to the present invention.

The preferred embodiments of the present invention will be discussed hereinafter in detail with reference to the accompanying drawings.

Firstly, discussion will be given for a gas collecting system to be applied to a method analyzing the formaldehyde in the ambient air according to the present invention. The gas collecting system 10 includes:

a portable air pump 12 basically driven by a portable battery for sucking gas in an inspection objective space;

an impinger 14 as a collecting vessel in which a collecting liquid 28 for collecting an inspection objective gas from the foregoing gas is filled;

a tube 24 having one end connected to the impinger 14 and the other end communicated with the foregoing inspection objective space, the tube 24 serving as an induction flow passage which introduces the foregoing gas into the impinger 14;

a tube 26 having one end connected to the foregoing impinger 14 and the other end connected to a suction port 12a of the foregoing air pump 12, the tube 26 serving as a suction flow passage which introduces the foregoing gas in the impinger 14 into the air pump 12;

a bag 18 connected to a discharge port 12b of the air pump 12 and accumulating the foregoing gas discharged from the air pump 12, the bag 18 serving as a storage body operating as a volumeter;

a drying agent tube 16 disposed between the bag 18 and the impinger 14 and serving as drying means for drying the foregoing gas;

a pressure switch 30 detecting an internal pressure of the foregoing bag 18;

a tube 36 as a bypass passage connecting the foregoing bag 18 to the foregoing suction port 12a of the foregoing air pump 12 bypassing the foregoing impinger 14;

a switching cock 34 serving as switching means for switching a flow passage connecting the foregoing bag 18 to either one of the foregoing discharge port 12b of the foregoing air pump 12 or the foregoing tube 36, and in conjunction therewith, connecting the discharge port 12b of the air pump 12 to the ambient air communication passage 38 when the bag 18 is connected to the tube 36;

a main receptacle box 40 receiving the foregoing air pump 12 and the foregoing battery therein, and in conjunction therewith, having mounting surfaces 40a and 40b on the outer surface for mounting the foregoing drying agent tube 16 and the foregoing impinger 14; and an auxiliary receptacle box 42 mounted on the main receptacle box 40, receiving the foregoing switching cock 34 and the foregoing pressure switch 30 therein and having a mounting portion 46 for detachably mounting the foregoing bag 18. The impinger 14 is formed of a transparent material and is used as a color comparison tube, and also as a reaction tube to be filled with reagents reacting with the inspection objective gas. The pressure switch 30 detects the internal pressure of the bag 18 when the predetermined pressure is reached, and outputs a stop signal to the air pump 12. Also, the bag 18 is foldable and exchangeable.

Discussing in detail, the shown embodiment of the gas collecting system 10 is a type sucking the ambient air, and includes the portable air pump 12 as shown in FIG. 1. By sucking the ambient air in the inspection objective space by the air pump 12, the inspection objective gas in the ambient air is taken in. The foregoing air pump 12 is portable and is driven by a portable battery, such as a dry cell or the like. In the suction port 12a of the air pump 12, the impinger 14 and the drying agent tube 16, which is also used as a filter, are provided in sequential order. Also, in the discharge port 12b of the air pump 12, the bag 18 accumulating the gas discharged from the discharge port 12b is provided. The bag 18 is used as a volumeter measuring the gas amount. On the other hand, on the downstream side of the drying agent tube 16, a check valve 20 permitting only flow of gas in a direction toward the suction port 12a of the air pump 12 is provided.

The impinger 14 is formed by a bottomed cylindrical glass tube in a test-tube-like configuration, of which an opening portion on the upper end is closed by an elastic cap 22. The tube 24 for introducing the ambient air and the tube 26 connecting the interior of the impinger 14 to the suction port 12a are provided in the impinger 14. These tubes 24 and 26 are formed by injection-needle-like metallic capillaries. Then, the tubes 24 and 26 formed by metallic capillaries are pierced into the elastic cap 22, and the respective needle-shaped tip end portions 24a and 26a are inserted into the impinger 14. Further, a predetermined amount of the collecting liquid 28 is filled into the impinger 14. The tip end portion 24a of the tube 24 is dipped into the collecting liquid 28, and in conjunction therewith, the tip end portion 26a of the tube 26 is located above the liquid surface of the collecting liquid 28.

The pressure switch 30 is provided between the air pump 12 and the bag 18. The pressure within the bag 18 is detected by the pressure switch 30. At a point of time in which the bag 18 is filled with air, the air pump 12 is stopped.

On the downstream side of the pressure switch 30, a switching cock 34 is provided in the discharge tube 32 communicated with the bag 18. The switching cock 34 connects the bag 18 to the discharge tube 32 of the air pump 12 when set at normal position shown in FIG. 2(a), and connects the bag 18 to the tube 36 bypassing the impinger 14 when set at the switched position shown in FIG. 2(b). At the switched position of the switching cock 34, the discharge pipe 32 is communicated with the ambient air communication passage 38.

Figure 3:
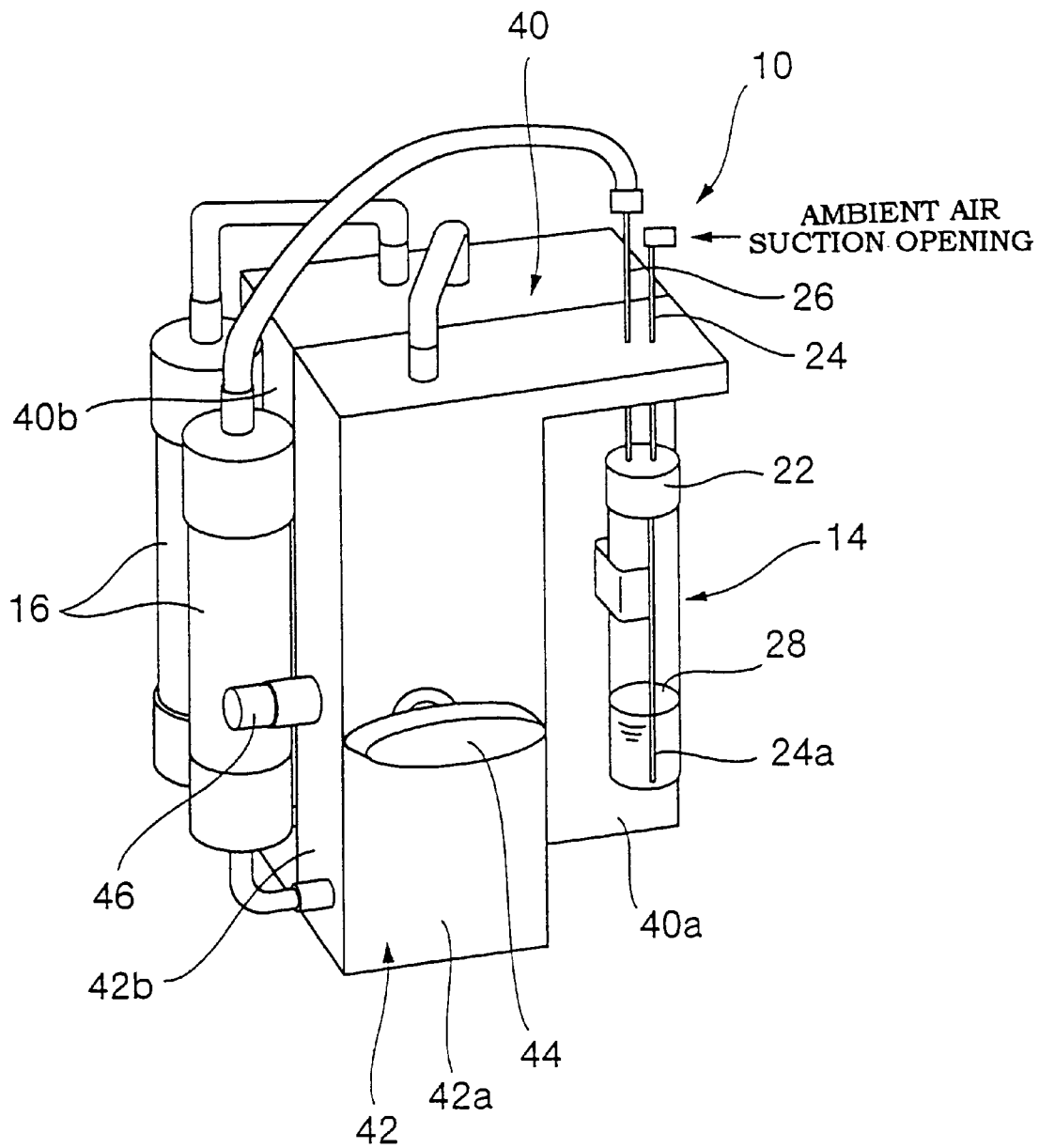
FIG. 3 is a perspective view showing an assembled condition of the gas collecting system shown in FIG. 1.

The gas collecting system 10 constructed as set forth above, is assembled into a compact construction as shown in FIG. 3. Namely, the auxiliary receptacle box 42 receiving the switching cock 34, the pressure switch 30 and so forth, is mounted onto the side surface 40a, which is the near side of the main receptacle box 40 receiving the air pump 12 and the dry cell or so forth as the driving source, with occupying approximately half of the space. A lever 44 of the switching cock 34 is provided projecting from the side surface 42a, which is the near side of the auxiliary receptacle box 42. Further, a mounting portion 46 of the bag 18 is provided on the side surface 42b, which is located on the side. Two drying agent tubes 16 are mounted on the side surface 40b, which is the side of the main receptacle box 40. The impinger 14 is mounted on a position on the side of the auxiliary receptacle box 42 on the side surface 40a, which is the near side of the main receptacle box 40. For example, the gas collecting system 10 is formed in a size having 10 cm in depth, 12 cm in width and 18 cm in height.

In the shown embodiment of the gas collecting system 10 constructed as set forth above, by driving the air pump 12, the ambient air in the measuring site is introduced into the impinger 14 through the tube 24, and is bubbled through the collecting liquid 28 in the impinger 14, and then sucked into the air pump 12 through the drying agent tube 16. The gas discharged from the air pump 12 is accumulated in the bag 18. Then, by using the bag 18 as the volumeter, the pressure switch 30 is actuated to stop the air pump 12 and terminate the collecting operation of the inspection objective gas when the bag 18 is full. At this point, the inspection objective gas in the ambient air is admixed with the collecting liquid 28 of the impinger 14, letting the impinger 14 perform inspection by functioning as a reaction vessel and the color comparison tube.

After completion of one cycle of the collecting operation, by setting the switching cock 34 at the switched position shown in FIG. 2(b), the bag 18 is connected to the suction port 12a of the air pump 12. The gas in the bag 18 is then sucked by the air pump 12 to be discharged automatically, making the bag empty for preparation for the next collection.

Here, the condensation rate of the gas component of the inspection objective gas in the collecting liquid 28 collected by the impinger 14 is determined by a ratio between the collecting liquid amount and the sucked ambient air amount. Since the impinger 14 is formed compact, condensation and collection can be done by a small amount (1 to 3 ml) of collecting liquid. Therefore, high condensation can be obtained with small amount of ambient air suction, and the volume of the bag 18 can be as small as 1 to 5 liters. Further, upon colorimetric analysis described above, since the impinger 14 can be used as the reaction vessel and color comparison tube as it is, the operation for transferring the collecting liquid 28 or for sampling a part of the collecting liquid 28 for analysis becomes unnecessary, thereby improving the operability in chemical analysis. Here, calorimetric analysis means an analyzing method performed by adding a reagent to the solution into which the inspection objective gas is collected, developing a particular color by chemical reaction, measuring light transparency by color density, and determining concentration of gas component. Commercial small size glass test tubes can be used for the impinger 14, permitting simple handling at quite a low cost in comparison with the conventional impinger.

The elastic cap 22 is fitted on the impinger 14, and large size injection needle-form metallic capillaries are employed for the tube 24 and the tube 26 to be set to the elastic cap 22. These tubes 24 and 26 can certainly provide flow passages for the air by simply piercing through the elastic cap 22. Since the impinger 14 may be operated in a condition where the elastic cap 22 is maintained in a fit-condition, the collecting liquid 28 will not spill even if the impinger is erroneously turned over. In addition, since the collecting liquid 28 and the reagents for reaction can be filled into the impinger 14 while maintaining the elastic cap 22 in the set condition, operability and security can be improved. Since the tube 24 and the tube 26 are constructed as capillaries, they have small diameters, and the bubbles discharged from the tip end of the tube 24 into the collecting liquid 28 becomes smaller, thereby enhancing the dissolving ability of the gas component and thus improving collection efficiency.

Furthermore, upon releasing the tube 24 and the tube 26 after completion of the collecting operation of the inspection objective gas, the interior pressure of the impinger 14 is slightly lowered, and the collecting liquid 28 residing within the tube 24 is suck into the impinger 14. Therefore, washing of the tube 24 and tube 26 becomes unnecessary. Also, contamination by the residual liquid can be prevented. In addition, the tip ends of the tube 24 and the tube 26 are formed as closed needles to facilitate insertion into the elastic cap 22. Communication openings for the gas are formed as transverse holes in the vicinity of the tip end portion 24a and 26a so as to prevent plugging by tip of the rubber.

As set forth above, the shown embodiment of the gas collecting system 10 has a simple construction, wherein the impinger 14 and the drying agent tube 16 are provided in the suction port 12a of the portable air pump 12, and the bag 18 is provided in the exhaust port 12b. Therefore, as shown in FIG. 3, these components can be assembled into a compact construction as a whole. Accordingly, the gas collecting system 10 assembled as set forth above is portable and is provided with superior transporting ability. Furthermore, adjustment on assembling the components thereof is not needed, and simple collection of the air at any site is possible. Therefore, handling can be simplified and will require no skill, permitting anybody's use. In this case, by mounting the system on a tripod for cameras or so forth, adjustment of height can be done easily, and the shown system requires less space. Accordingly, the gas collecting system 10 is quite simple in construction and is inexpensive and compact.

Figure 2:
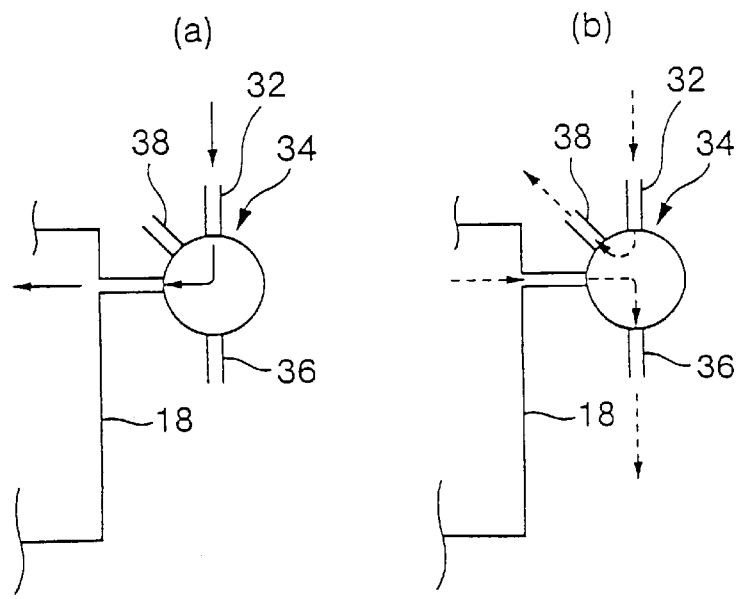
FIG. 2 is an explanatory illustration of a switching cock provided in the gas collecting system shown in FIG. 1.

Furthermore, the method for analyzing formaldehyde in the ambient air according to the present invention is to perform sampling of the air of the building site and to measure the concentration of formaldehyde by employing the gas collecting system 10, as shown in FIGS. 1 to 3, so that formaldehyde can be easily analyzed from the gas collected by the gas collecting system 10. In the analyzing method according to the present invention, the members, such as the impingers 14 which are exchangeable consumable articles, and chemicals can be supplied as an analysis kit.

The analysis kit to be used when implementing the first embodiment of the method for analyzing formaldehyde in the ambient air according to the present invention is to be provided with:

(i) ten to twenty impingers 14 respectively filled with 2.0 ml of collecting liquid 28, wherein 2N—KOH solution (aqueous sodium hydroxide of 2 normals) is employed as the collecting liquid 28;
(ii) one Vial bottle A (having a volume of 50 to 100 ml) containing AHMT reagent;
(iii) one vial bottle B (having a volume of 50 to 100 ml) containing $KIO_4$ reagent;
(iv) several plastic injectors (having a volume of 1 ml);
(v) one impinger containing a standard color solution;
(vi) one sand glass (for 20 minutes use); and (vii) one portable absorptiometer.

Next, discussion will be made about the operating procedure for measurement of the concentration of formaldehyde by employing the foregoing analysis kit.

(I) First, the impinger 14 is mounted on the gas collecting system 10 to suck the gas containing formaldehyde. At this time, the standard gas suction amount is 3 liters, and the standard required time is estimated as 10 minutes.

(II) 0.5 ml of AHMT reagent is taken from the vial bottle A by the injector and added to the impinger 14. The impinger is left in this condition for 15 to 20 minutes or longer. At this time, the sand glass is used.

(III) While adding AHMT reagent to the impinger 14 and leaving the same, the standard color solution is set to the absorptiometer. Then, a dial is adjusted so that the indication value comes to a predetermined value.

(IV) 0.5 ml of $KIO_4$ reagent is taken from the vial bottle B by the injector and added to the impinger 14.

(V) The impinger 14 is set to the absorptiometer so that the indication value is read, and the read value is obtained as the concentration of formaldehyde.

Accordingly, in the analysis method of formaldehyde according to the first embodiment, the impinger 14 (i) used in the analysis kit can efficiently collect formaldehyde in the gas and enhances the collection efficiency, since 2N—KOH solution is used. In addition, since the amount of collecting liquid 28 used is small as 2.0 ml, high condensation can be achieved even with small suction amount of the gas, which facilitates detection even in low gas concentration. This is an appropriate concentration for certainly maintaining the reaction ability of the AHMT reagent (ii) added afterwards, and thus, it becomes unnecessary to add alkaline reagents.

On the other hand, the concentrations of the AHMT reagent and the $KIO_4$ reagent necessary for analysis are set so that an optimal reaction condition is obtained with respect to the collecting liquid 28 and so that the liquid amount being added by the injector can be small. Namely, the AHMT reagent is prepared to have a composition of AHMT:1%, and HCl:1 mol/liter, and the $KIO_4$ reagent is prepared to have a composition of $KIO_4$:1% and KOH:0.25N.

The adding amount of both regents are set to be appropriate at 0.5 ml. This is because lower concentration conventionally used required about four times of adding amount, which lowered sensitivity of detection and the color development since the overall liquid amount increased. On the other hand, when adding amount of the reagent is extremely reduced, the reading error upon measuring of the liquid amount by the injector becomes large. In the shown embodiment, since the amount of both reagent used at one time is small as 0.5 ml, analyses can be implemented many times even when the amount of the reagents carried are small.

Further, both reagents are contained in the vial bottles A and B of (ii) and (iii), and made into kits. Since these vial bottles are bottles with rubber caps used for injectors, the reagents can be measured and taken by the injector without removing of the caps. Therefore, the reagent will not spill or be deposited onto the hand.

Next, the standard color solution described in (v) is preliminarily prepared in a laboratory by taking a standard colored liquid corresponding to a color development density developed upon reaction of a known amount of formaldehyde with the reagent, and is enclosed in the same container as the impinger 14.

By enclosing the standard color solution in the impinger 14, and by adjusting the colorimeter (absorptiometer) with taking the absorbance of the standard colored liquid as a standard upon absorbance measurement, it becomes unnecessary to prepare an analytical curve by actually performing reaction of a known amount of the formaldehyde liquid for each analysis. Also, since the color development density of the colored liquid developed by reacting formaldehyde becomes unstable and the color gradually turns dilute according to elapsed time, the standard colored liquid is prepared by using a red color dye having less fading.

On the other hand, since the color collecting system 10 has a construction which can constantly suck a predetermined amount of gas, by adjusting the indication value of the absorptiometer to a predetermined value by using the standard colored liquid under a premise of the suction gas amount, the indication value of the unknown sample can be directly read as the concentration of the formaldehyde upon measurement of absorbance. Accordingly, calculation using molecular weight of formaldehyde and volume conversion coefficients as gas or so forth becomes unnecessary. Also, as for the portable absorptiometer of (vii), a compact and lightweight one operated by a dry cell is used, and it has a perimselective filter of wavelength 530 nm.

Accordingly, in the shown embodiment, since formaldehyde concentration is measured by sucking the gas by the gas collecting system 10 by employing the impinger 14, the AHMT reagent, $KIO_4$ reagent, the injector, the standard color solution, the sand glass and the portable absorptiometer forming the kit, the system can be made compact to be easily handled and requires no special device. Thus, a result can be obtained within a short period of time at the site where the gas is collected. On the other hand, expert knowledge and chemical calculation becomes unnecessary, and also, transferring or division of the sampled solution becomes unnecessary. Therefore, there is no need for special measuring equipment (such as transfer pipettes or the like) for chemical analysis, which require skill in handling.

The collecting liquid 28 and the reagents can be taken by the injector without releasing the cap. Therefore, even if the bottle is turned over, the content will never be spilled, thereby permitting safe operation. In addition, since analysis can be performed at the gas sampling site, it becomes unnecessary to pay any attention for transportation of the sample. Also, it becomes unnecessary to rely on an outer analyzing organization requiring high cost. Since result can be obtained immediately at low cost, measurements can be performed many times sequentially along with observation of the results.

As set forth above, in the shown embodiment of the formaldehyde analyzing method, no expert knowledge is required in measurement of concentration of formaldehyde, and this permits simple and easy operation at low cost and within a short period of time. Therefore, even when inspection is performed within a new building, a large amount of inspection data, such as amount of formaldehyde generated from various construction materials, and amount of formaldehyde present in the room environment, can be obtained.

In the shown embodiment, it is possible to simply measure the formaldehyde concentration, and also obtain the equal results compared with the conventional analyzing method as shown in Table 1 below. Namely, Table 1 is prepared by measuring formaldehyde concentration of indoor air within an actual dwelling unit. As a comparative prior art, the results of an analysis by means of high performance liquid chromatograph well known as a high-level analyzing method is shown.

TABLE 1

Result of actual measurement of
formaldehyde concentration
in an indoor air

| Data No. | Method of the present invention | Precise method in the prior art |
|---|---|---|
| 1 | 0.220 ppm | 0.23 ppm |
| 2 | 0.190 ppm | 0.19 ppm |
| 3 | 0.128 ppm | 0.14 ppm |
| 4 | 0.115 ppm | 0.12 ppm |

In the table above, four data (No. 1 to 4) are indicated, each of which having a condition different from each other in the inspection dwelling unit and the inspection time zone. In the method of the shown embodiment, the gas collecting system 10 is employed to suck 3 liters of the air for about 10 minutes, and the data analyzed in the building site using an analysis kit is applied. On the other hand, in the conventional method, a commercial DNPH cartridge for collecting the formaldehyde is employed to suck 25 to 30 liter of the air for about 30 minutes, and the cartridge is transported by means of a cold storage vessel to an analyzing organization. The data obtained by means of HPLC (high performance liquid chromatograph) after solvent-extraction are listed.

Figure 4:
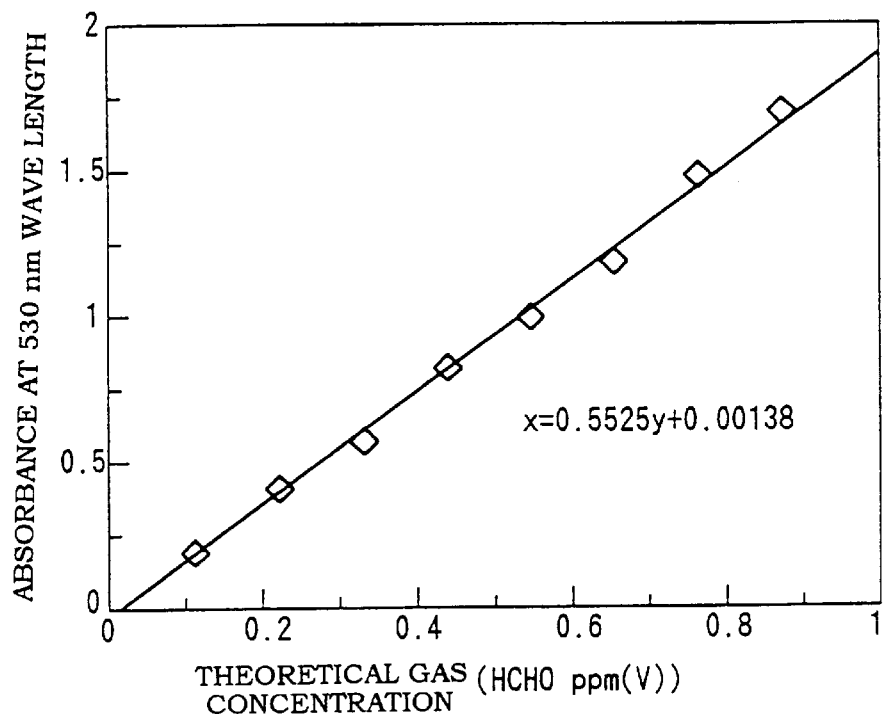
FIG. 4 is a characteristic diagram of an analytical curve showing the relationship between the gas concentration and absorbance obtained by the method for analyzing formaldehyde in the ambient air of the present invention.

FIG. 4 is an illustration of one example of an analytical curve showing the relation between formaldehyde concentration and absorbance by employing the analysis kit of the shown embodiment. The vertical axis (y) represents the color density of the reaction product of the formaldehyde shown as the absorbance at 530 nm wavelength, and the transverse axis (x) represents the theoretical formaldehyde concentration (volume ppm) in case of taking 3 liters of air suction and by using a concentration-known formaldehyde liquid. The graph shows these correlation. By this graph, the following regression equation can be derived.

$$x = 0.5525y + 0.00138$$

Therefore, it can be understood that a linear relationship is established between the gas concentration and absorbance, and thus the shown embodiment has the performability to sufficiently detect the formaldehyde concentration in practical range.

Figure 5:
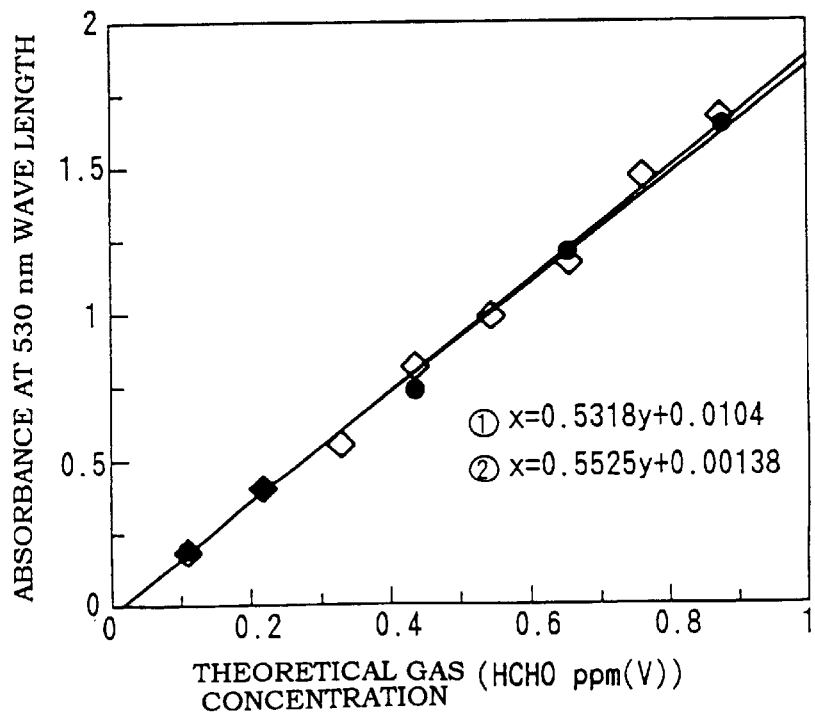
FIG. 5 is a comparative characteristic diagram of the analytical curves measured on different days by the method for analyzing formaldehyde in the ambient air of the present invention.

FIG. 5 is an illustration of one example of a comparison of the analytical curve being measured twice on different testing days (black circle indicates the one measured later). From FIG. 5, it can be understood that the repeatability of the measured value is excellent. The meanings of the vertical axis and the transverse axis of the graph are the same as those of the graph of FIG. 2.

Figure 6:
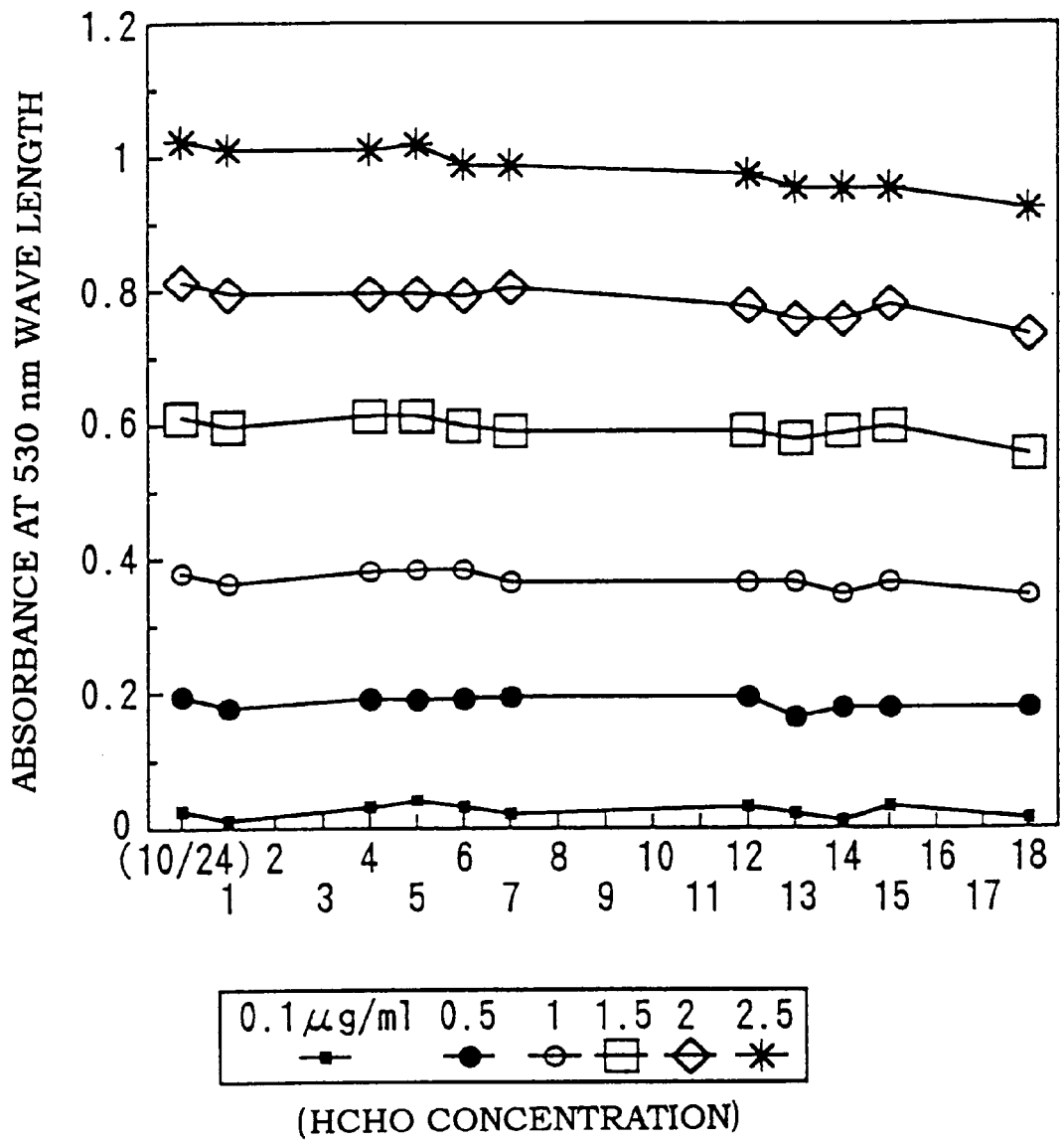
FIG. 6 is a characteristic diagram showing the stability of the color development of a collecting liquid relative to the elapsed time according to the method for analyzing formaldehyde in the ambient air of the present invention.

Furthermore, FIG. 6 is an illustration showing a data example for confirming the stability of the color development liquid after developing of color. From FIG. 6, it can be understood that it is unnecessary to measure the absorbance (concentration) immediately after developing the color, but the measurement after a long time elapsed is undesirable. Therefore, the standard color solution included in the analysis kit is to be prepared using a stable dye. Here, the vertical axis presents the color density of the reaction product of the formaldehyde shown as the absorbance at 530 nm wavelength, and the transverse axis represents the elapsed number of days. Furthermore, formaldehyde concentration is indicated in $\mu g/ml$.

In the second embodiment of the formaldehyde analyzing method, the analysis kit is provided with:
(i) ten to twenty impingers 14 respectively filled with 2.0 ml of 2N—NaOH solution (aqueous sodium hydroxide of 2 normals) employed as the collecting liquid 28;
(ii) one vial bottle A (having a volume of 50 to 100 ml) containing AHMT reagent prepared using $HClO_4$;
(iii) one vial bottle B (having a volume of 50 to 100 ml) containing $KIO_4$ reagent;
(iv) several plastic injectors (having a volume of 1 ml);
(v) one impinger containing a standard color solution;
(vi) one sand glass (for 20 minutes use); and
(vii) one portable absorptiometer.

On the other hand, the concentrations of the AHMT reagent and the $KIO_4$ reagent necessary for analysis are set so that an optimal reaction condition is obtained with respect to the collecting liquid 28, and so that the liquid amount to be added by the injector can be small. Namely, the AHMT reagent is prepared to have a composition of AHMT:1%, and $HClO_4$:4 to 5%, and the $KIO_4$ reagent is prepared to have a composition of $KIO_4$:1% and KOH:0.2 to 0.3 N.

The operation procedure for measuring formaldehyde concentration by means of the foregoing analysis kit is the same as that of the first embodiment.

On the other hand, in the second embodiment, the following matters are considered in regard of the collecting liquid 28 and the AHMT reagent. Since AHMT reagent cannot be dissolved without adding acid, it is normally dissolved by adding HCl. The reagent is sampled by the injector as set forth above in order to improve operability upon handling. However, by repeatingly sampling the HCl-added AHMT reagent with the injector, corrosion of the injection needle may be caused by the effect of HCl. Thus, the life of the needle is considered to be quite short. Also, the reagent may be contaminated by eluted substance from the needle, such as iron ion produced by corrosion of the needle, which may possibly cause error in analysis. Therefore, in the shown second embodiment, $HClO_4$ is used in place of HCl for dissolving AHMT reagent. In this way, corrosion of the injection needle and contamination of the reagent can be avoided. On the other hand, in addition to the foregoing 2N—NaOH, 2N—KOH (potassium hydroxide solution of 2 normals) may be employed as the collecting liquid 28. However, when $HClO_4$ is employed in the AHMT reagent, and at the same time 2N—KOH is employed as the collecting liquid 28, $HClO_4$ and KOH react to produce potassium perchlorate at the time when the AHMT reagent is added to the collecting liquid 28. Potassium perchlorate is difficult to be dissolved in water, and causes white turbidity of the sample solution. Therefore, considering that $HClO_4$ is used for the AHMT reagent, 2N—NaOH is employed as the collecting liquid 28.

In either analyzing method of the first or second embodiments, AHMT reagent is added to the collecting liquid 28 after the gas collecting operation, and subsequently, $KIO_4$ reagent is added. Here, an embodiment of an analyzing method for formaldehyde which can further simplify the analyzing method will be discussed.

In this case, the analysis kit is provided with:
(i) ten to twenty impingers 14 normally filled with 2 to 3 ml of the collecting liquid 28 which is a 2N—KOH solution or a 2N—NaOH solution;
(ii) one impinger containing the standard color solution;
(iii) several plastic injectors (having volume of 1 ml); and
(iv) one portable absorptiometer.

Particularly, the shown embodiment is designed to eliminate the operation for adding the reagent after completion of collection and the waiting time for the reaction process, by causing the color development reaction while collecting the formaldehyde gas. Therefore, in the shown embodiment, the collecting liquid 28 is prepared by mixing an alkaline reagent and a reducing reagent, such as sodium hyposulfite and so forth, at an appropriate mixing ratio.

In the conventional method, three kinds of reagents, the alkaline reagent, the AHMT reagent, and $KIO_4$ reagent, are used separately. In the case where these reagents are preliminarily mixed, normal reaction with formaldehyde cannot be caused. Therefore, it becomes necessary to add them separately in a predetermined sequential order and by keeping time interval required for reaction.

In contrast to this, when the collecting agent 28 of the shown embodiment is employed, it becomes possible to add AHMT liquid to the collecting liquid 28 before gas collecting operation, and the $KIO_4$ reagent becomes unnecessary.

Then, since AHMT reagent can be added in advance, color development reaction can be caused along with the gas collection, and the gas collecting operation can be performed while visually monitoring the condition thereof. Since color development reaction is progressed along with the gas collection, it becomes possible to omit the waiting period for the reaction caused by adding the AHMT reagent after gas collection. Furthermore, although $KIO_4$ reagent is required to generate a red colored substance by oxidizing the reaction intermediate product of AHMT reagent and formaldehyde, since AHMT reagent can be added in advance, the oxygen in air introduced into the collecting liquid 28 during the process of gas collection serves as an oxidation agent and functions as a replacement for $KIO_4$ reagent. Therefore, $KIO_4$ reagent becomes unnecessary.

Next, the operation procedure in measurement of formaldehyde concentration using the analysis kit will be discussed hereinafter.

In this case, the procedure is quite simple.

(I) 0.5 ml of AHMT solution is added by the injector to the impinger 14 containing the collecting liquid 28, then gas is sucked. At this time, the standard gas suction amount is 3 liters, and the standard required time is 10 minutes.

(II) The impinger 14 is set to the absorptiometer, and the indication value is read, and the read value is obtained as the formaldehyde concentration.

Namely, in the shown embodiment, a given amount of collecting liquid 28, which is prepared by mixing the alkaline reagent and the reducing reagent such as sodium hyposulfite and so forth at an appropriate mixing ratio, is filled in the impinger 14. Then, the given amount of the gas in the inspection objective space is passed through the impinger 14. In conjunction therewith, the standard color solution is set to the absorptiometer for adjusting the indication value to a predetermined value. Then, the impinger 14 is set to the absorptiometer, and an analysis is made by detecting formaldehyde concentration from the indication value.

Not to mention, in the preferred embodiment set forth above, it is also possible to obtain the same operation and effect as those of the foregoing first and second embodiments.

Figure 7:
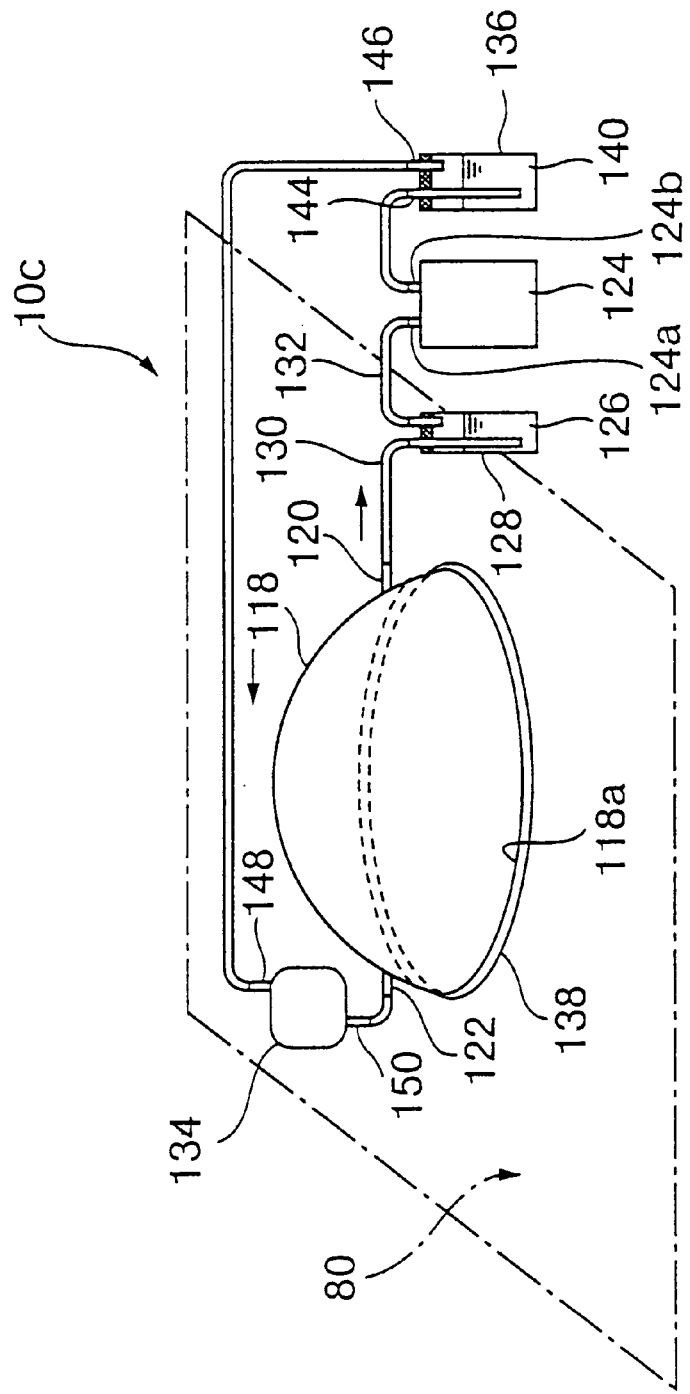
FIG. 7 is a circuit diagram of another embodiment of a gas collecting system applicable to the method for analyzing formaldehyde in the ambient air according to the present invention.

FIG. 7 is an illustration of another embodiment of the gas collecting system 10c which is applicable to the method for analyzing formaldehyde in the ambient air according to the present invention. The gas collecting system 10c is a type in which the inspection objective gas is collected while the gas in the inspection objective space enclosed by a casing 96 is circulated within a closed loop circuit.

The gas collecting system 10c has a casing 118 formed into a hemisphere-shape with a transparent material having a given thickness for collecting the inspection objective gas naturally discharged from the inspecting portion. Around the casing 118, an impinger 128, an air pump 124, a humidity conditioner bottle 136 and a buffer 134 are connected in sequential order to form a closed flow passage for circulating the gas so that the gas in the casing 118 is forcedly sucked by the air pump 124 and is circulated to collect the inspection objective gas with the impinger 128.

In the casing 118, a gas circulating port 122 for taking in the circulating gas, and a gas circulating port 120 feeding the gas mixed with the inspection objective gas from the casing 118, are provided in opposed position. A packing 138 formed of soft rubber or the like is mounted on the peripheral edge of the opening 118a of the casing 118. The packing 138 is abut onto the surface of the inspection object 80 to sealingly enclose the interior of the casing 118.

The impinger 128 filled with the collecting liquid 126, the tube 130 introducing gas thereinto, and the tube 132 thus feeding out the gas are similar to the impinger 14, the tubes 24 and 26 described in the first embodiment.

The air pump 124 is portable and driven by a battery, such as a dry cell or the like, similar to the first embodiment. The suction port 124a is connected to the impinger 128 via the tube 132, and the discharge port 124b is connected to a humidity conditioner bottle 136.

The humidity conditioner bottle 136 is formed by a cylindrical glass bottle. The upper end opening portion is closed by a rubber cap. A predetermined amount of a humidity conditioner 140, which is of a saline solution, is filled in the humidity conditioner bottle 136. The tip end of a tube 144 provided on the side introducing the gas is extended into the liquid of the humidity conditioner 140. The tip end of a tube 146 provided on the side discharging the gas is extended above the liquid surface of the humidity conditioner 140, thereby causing bubbling of the introduced gas. The tube 144 is connected to the discharge port 124b of the air pump 124, and the tube 146 is connected to an induction opening 148 of the buffer 134 to maintain the humidity of the gas circulated to the casing 118. Namely, as the humidity conditioner 140, a saturated solution of $BaCl_2.2H_2O$ can be used as the saline solution. By passing air through the saturated solution, air containing 88% of humidity is obtained at 24.5° C., and the humidity of the passing air is maintained at the predetermined value. This is because the humidity of the air in contact with the saline solution indicates a constant value, according to the kind and concentration of the salt and temperature, in relation to the vapor pressure of the saline solution. Since the values of the relationship with respect to various salts are disclosed in chemical handbooks or the like, the salts may be appropriately selected depending upon the desired humidity.

The buffer 134 is formed with a plastic film or the like and is shaped like a bag variable of volume. In the buffer 134, an induction opening 148 introducing a flowing gas, and a discharge opening 150 feeding out the interior gas are provided in opposed position. The induction opening 148 is connected to the tube 146 coming from the humidity conditioner bottle 136, and in conjunction therewith, the discharge opening 150 is connected to the gas circulating portion 122 of the casing 118 so that it may be expand and vary the volume of the buffer depending upon the difference between the gas pressure introduced thereinto and the ambient air pressure. Namely, when the internal pressure is elevated, the buffer is expanded, and when the internal pressure is reduced, the buffer is contracted, making the pressure difference between the inside and the outside to naturally be zero, and this enables circulation without causing variation in pressure of the gas.

Then, in this gas collecting system 10c, the opening 118a of the casing 118 is abut onto the inspection object 80, and in conjunction therewith, the air pump 124 is driven. At this time, since the packing 138 is provided on the opening 118a of the casing 118, the abutted portion is sealingly enclosed by abutting the packing 138 onto the surface of the inspection object 80. Further, since the casing 118 is formed transparent, the setting condition can be checked, and the condition of the surface of the inspection object 80 can be easily observed. Since the gas is sucked by the air pump 124, the gas within the casing 118 is introduced into the impinger 128, and is bubbled through the collecting liquid 126 in the impinger 128 to be sucked into the air pump 124. The sucked gas is discharged from the discharge portion 124b of the air pump 124 to be returned to the interior of the casing 118 through the humidity conditioner bottle 136 and the buffer 134 for circulation. At this time, the inspection objective gas from the inspection object 80 is discharged from the inside of the enclosed casing 118, and is captured in the collecting liquid 126 by bubbling through the collecting liquid 126 of the impinger 128. Then, the gas returned within the casing 118 from the buffer 134 is purified since the inspection objective gas is captured by the impinger 128. Also, the humidity thereof is maintained constant by the humidity conditioner bottle 136.

Thus, collection of the inspection objective gas is performed for a predetermined period of time by circulating the gas and by collecting the inspection objective gas, whereby an analysis is performed by a chemical method to determine the amount of the inspection objective gas contained in the collecting liquid 126 of the impinger 128. At this time, the amount of gas discharged can be derived by the following equation (1).

$$\text{discharge amount of inspection objective gas} = \text{collected gas amount}/(\text{opening area of casing} \times \text{period of collecting operation}) \quad (1)$$

The shown embodiment of the gas collecting system 10c can perform inspection for construction materials alone, and as well, can collect the inspection objective gas of the material already in use, namely, of any portion of a building after construction is completed.

As set forth above, according to the method for analyzing formaldehyde in the ambient air of the present invention, the formaldehyde gas can be efficiently collected by the collecting liquid, by passing the gas to be inspected through the collecting vessel filled with 2N—KOH solution or 2N—NaOH solution as the collecting liquid.

Since the analysis is implemented by using AHMT reagent and $KIO_4$ reagent, the optimal reaction condition can be obtained with respect to 2N—KOH solution or 2N—NaOH solution, and therefore the accuracy of analysis can be enhanced.

Further, by using 2N—NaOH solution as the collecting liquid, and using $HClO_4$ for dissolving the AHMT reagent, corrosion of the injection needle can be avoided and contamination of the reagent can be prevented. Moreover, since 2N—NaOH is used as the collecting liquid considering that $HClO_4$ is also used for AHMT reagent, it is possible to avoid causing white turbidity of the sample solution.

Furthermore, the standard colored liquid, which corresponds to a color development density upon reaction of a known amount of formaldehyde with a reagent, is prepared as the standard color solution, and the absorptiometer is adjusted by taking the absorbance of this standard colored liquid as a standard upon absorbance measurement. Therefore, the complicated operation for preparing an analytical curve by actually performing reaction of a known amount of the formaldehyde liquid per analysis becomes unnecessary.

Furthermore, by adjusting the absorptiometer to a predetermined value by the use of the standard colored liquid under a premise that a given amount of air passes through the reaction vessel, the indication value of the unknown sample can be directly read as the concentration of the formaldehyde upon measurement of absorbance. Accordingly, calculation using molecular weight of formaldehyde and volume conversion coefficients as gas or so forth becomes unnecessary, and expert knowledge and chemical calculation becomes unnecessary. Also, transferring or division of the sampled solution becomes unnecessary, therefore requiring no skill in handling.

Therefore, according to the analyzing method of the present invention, an accurate result can be obtained within a short period of time at the site where the gas is collected.

What is claimed is:

1. A method for analyzing a concentration of formaldehyde in air, comprising:

passing a given amount of said air through a collecting vessel comprising a given amount of an alkaline solution, said collecting vessel being filled with said given amount of said alkaline solution before passing said given amount of said air;

filling a given amount of an AHMT reagent into said collecting vessel and leaving said reagent in said collecting vessel for a given period of time;

using a standard color solution for calibrating an indication value of an absorptiometer to a predetermined value;

adding a given amount of $KIO_4$ to said collecting vessel; and setting said collecting vessel in said absorptiometer to detect said formaldehyde concentration from a value of the indication value of said absorptiometer, wherein said concentration of formaldehyde is directly indicated by the value of the indication value of said absorptiometer.

2. The method for analyzing the formaldehyde concentration in air as set forth in claim 1, wherein said alkaline solution is a 2N—KOH solution and said collecting vessel is filled with 2.0 ml or less of said 2N—KOH solution.

3. The method for analyzing the formaldehyde concentration in air as set forth in claim 1, wherein said collecting vessel is filled with substantially about 0.5 ml of said AHMT reagent and said $KIO_4$ reagent.

4. The method for analyzing the formaldehyde concentration in air as set forth in claim 1, wherein a composition of said AHMT reagent is AHMT:1%, and HCl:1 mol/liter, and a composition of said $KIO_4$ reagent is $KIO_4$:1% and KOH:0.25N.

5. The method for analyzing the formaldehyde concentration in air as set forth in claim 1, wherein said standard color solution is a standard colored liquid prepared by using a red color dye corresponding to a color development density developed upon reaction of a known amount of formaldehyde with a reagent.

6. The method for analyzing the formaldehyde concentration in air as set forth in claim 1, wherein said alkaline solution is a KOH solution.

7. The method for analyzing the formaldehyde concentration in air as set forth in claim 1, wherein said alkaline solution is a 2N—KOH solution.

8. A method for analyzing a concentration of formaldehyde in air, comprising:

passing a given amount of said air through a collecting vessel comprising a collecting liquid prepared by adding a given amount of an AHMT solution to a given amount of an alkaline solution;

using a standard color solution for calibrating an indication value of an absorptiometer to a predetermined value;

setting said collecting vessel in said absorptiometer, and detecting said formaldehyde concentration from a value of the indication value of said absorptiometer, wherein said concentration of formaldehyde is directly indicated by the value of the indication value of said absorptiometer.

9. The method for analyzing the formaldehyde concentration in air as set forth in claim 8, wherein said alkaline solution is a KOH solution.

10. A method for analyzing a concentration of formaldehyde in air, comprising:

passing a given amount of said air through a collecting vessel comprising a given amount of an alkaline solution, said collecting vessel being filled with said given amount of said alkaline solution before passing said given amount of said air;

filling a given amount of an AHMT reagent prepared by using $HClO_4$ into said collecting vessel and leaving said reagent in said collecting vessel for a given period of time;

using a standard color solution for calibrating an indication value of an absorptiometer to a predetermined value;

adding a given amount of $KIO_4$ to said collecting vessel; and setting said collecting vessel in said absorptiometer to detect said formaldehyde concentration from a value of the indication value of said absorptiometer, wherein said concentration of formaldehyde is directly indicated by the value of the indication value of said absorptiometer.

11. The method for analyzing the formaldehyde concentration in air as set forth in claim 10, wherein said alkaline solution is a 2N—NaOH solution and said collecting vessel is filled with 2.0 ml or less of said 2N—NaOH solution.

12. The method for analyzing the formaldehyde concentration in air as set forth in claim 10, wherein said collecting vessel is filled with substantially about 0.5 ml of said AHMT reagent and said $KIO_4$ reagent.

13. The method for analyzing the formaldehyde concentration in air as set forth in claim 10, wherein a composition of said AHMT reagent is AHMT:1% and $HClO_4$:4 to 5%, and a composition of said $KIO_4$ reagent is $KIO_4$:1% and KOH:0.2 to 0.3N.

14. The method for analyzing the formaldehyde concentration in air as set forth in claim 10, wherein said standard color solution is a standard colored liquid prepared by using a red color dye corresponding to a color development density developed upon reaction of a known amount of formaldehyde with a reagent.

15. The method for analyzing the formaldehyde concentration in air as set forth in claim 10, wherein said alkaline solution is a NaOH solution.

16. The method for analyzing the formaldehyde concentration in air as set forth in claim 10, wherein said alkaline solution is a 2N—NaOH solution.

17. A method for analyzing a concentration of formaldehyde in air, comprising:

passing a given amount of said air through a collecting vessel comprising a collecting liquid prepared by adding a given amount of an AHMT solution prepared by using $HClO_4$ to a given amount of an alkaline solution;

using a standard color solution for calibrating an indication value of an absorptiometer to a predetermined value;

setting said collecting vessel in said absorptiometer, and detecting said formaldehyde concentration from a value of the indication value of said absorptiometer, wherein said concentration of formaldehyde is directly indicated by the value of the indication value of said absorptiometer.

18. The method for analyzing the formaldehyde concentration in air as set forth in claim 17, wherein said alkaline solution is a NaOH solution.

* * * * *